United States Patent
Heath

(10) Patent No.: US 6,497,709 B1
(45) Date of Patent: *Dec. 24, 2002

(54) METAL MEDICAL DEVICE

(75) Inventor: Kevin R. Heath, Weston, MA (US)

(73) Assignee: Boston Scientific Corporation, Natick, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/851,161

(22) Filed: May 5, 1997

Related U.S. Application Data

(63) Continuation of application No. 08/756,187, filed on Nov. 25, 1996, now abandoned, which is a continuation of application No. 08/527,749, filed on Sep. 13, 1995, now abandoned, which is a continuation of application No. 07/861,253, filed on Mar. 31, 1992, now abandoned.

(51) Int. Cl.⁷ .............................................. A61B 5/00
(52) U.S. Cl. ...................................................... 606/127
(58) Field of Search .............................. 600/433–436, 600/585; 604/95, 283; 606/127, 151, 200

(56) References Cited

U.S. PATENT DOCUMENTS

| | | |
|---|---|---|
| 2,524,661 A | 10/1950 | Harder et al. |
| 3,196,876 A | 7/1965 | Miller |
| 3,335,443 A | 8/1967 | Parisi et al. |
| 3,466,166 A | 9/1969 | Levinstein et al. |
| 3,528,410 A | 9/1970 | Banko |
| 3,558,066 A | 1/1971 | Alliger |
| 3,562,024 A | 2/1971 | Smith et al. |
| 3,584,327 A | 6/1971 | Murry |
| 3,589,363 A | 6/1971 | Banko et al. |
| 3,605,750 A | 9/1971 | Sheridan |

(List continued on next page.)

FOREIGN PATENT DOCUMENTS

| | | |
|---|---|---|
| CA | 1324533 | 11/1993 |
| DE | 33 29 176 | 11/1984 |
| DE | 40 22 956 | 2/1992 |
| DE | 92 06 170 | 5/1992 |
| EP | 0 067 929 | 12/1982 |
| EP | 0 121 447 | 10/1984 |
| EP | 0 221 570 | 5/1987 |
| EP | 0 405 429 A2 | 1/1991 |

(List continued on next page.)

OTHER PUBLICATIONS

US 5,040,280, 8/1991, Takada (withdrawn)
Klinger and Kurisky, "MP35N alloy—the ultimate wire material", *Wire Journal*, 1980.
Metals Handbook, Tenth Edition, vol. 1, ASM International, Materials Park, OH 1990.
Metals Handbook, Tenth Edition, vol. 2, ASM International, Materials Park, OH.
*Schneider, PCT/US93/11262 Search Report, Nov. 1993.
*Schneider, PCT/IB95/00253 Search Report, Oct. 1995.
*Sigwart et al., *The New England Journal of Medicine*, vol. 316, Mar. 19, 1987.
*"Strengthening Mechanisms in Elgiloy", *Journal of Materials Science* 19, pp. 2815–2836.
Alliger, "Ultrasonic Disruption", Am. Lab. (a journal), vol. 7, No. 10, 1975, pp. 75–76, 78, 80–82, 84 and 85.

(List continued on next page.)

Primary Examiner—Max Hindenburg
(74) Attorney, Agent, or Firm—Fish & Richardson P.C.

(57) ABSTRACT

A medical device and method for treatment in which the device has a portion for use within the body that exhibits enhanced properties such as radiopacity for viewing by x-ray fluoroscopy. The portion includes an extended metal outer member having, e.g., a predetermined density and an exposed outer surface and a core, including a metal having, e.g., a density greater than the outer member to enhance radiopacity, substantially enclosed by the outer member.

35 Claims, 4 Drawing Sheets

U.S. PATENT DOCUMENTS

| | | |
|---|---|---|
| 3,618,594 A | 11/1971 | Banko |
| 3,618,614 A | 11/1971 | Flynn |
| 3,749,086 A | 7/1973 | Kline et al. |
| 3,805,787 A | 4/1974 | Banko |
| 3,823,717 A | 7/1974 | Pohlman et al. |
| 3,830,240 A | 8/1974 | Antonevich et al. |
| 3,861,391 A | 1/1975 | Antonevich et al. |
| 3,896,811 A | 7/1975 | Storz |
| 3,930,173 A | 12/1975 | Banko |
| 3,941,122 A | 3/1976 | Jones |
| 3,942,519 A | 3/1976 | Shock |
| 3,956,826 A | 5/1976 | Pardeaux, Jr. |
| 4,023,557 A | 5/1977 | Thorne et al. |
| 4,041,931 A | 8/1977 | Elliott et al. |
| 4,178,935 A | 12/1979 | Gekhman et al. |
| 4,188,952 A | 2/1980 | Loschilov et al. |
| 4,202,349 A | 5/1980 | Jones |
| 4,281,419 A | 8/1981 | Treace |
| 4,295,464 A | 10/1981 | Shihata |
| 4,345,602 A | 8/1982 | Yoshimara et al. |
| 4,351,326 A | 9/1982 | Kosonen |
| 4,370,131 A | 1/1983 | Banko |
| 4,380,574 A | 4/1983 | Gassinger et al. |
| 4,406,284 A | 9/1983 | Banko |
| 4,417,578 A | 11/1983 | Banko |
| 4,425,115 A | 1/1984 | Wuchinich |
| 4,425,908 A | 1/1984 | Simon |
| 4,464,176 A | 8/1984 | Wijayarathma |
| 4,465,481 A | 8/1984 | Blake |
| 4,474,180 A | 10/1984 | Angulo |
| 4,486,680 A | 12/1984 | Bonnet et al. |
| 4,504,268 A | 3/1985 | Herlitze |
| 4,517,793 A | 5/1985 | Carus |
| 4,518,444 A | 5/1985 | Albrecht et al. |
| 4,535,759 A | 8/1985 | Polk et al. |
| 4,553,545 A | 11/1985 | Maass et al. |
| 4,561,438 A | 12/1985 | Bonnet et al. |
| 4,572,184 A | 2/1986 | Stohl et al. |
| 4,577,637 A | 3/1986 | Mueller, Jr. |
| 4,580,568 A | 4/1986 | Gianturco |
| 4,600,446 A | 7/1986 | Torisaka et al. |
| 4,602,633 A | 7/1986 | Goodfriend et al. |
| 4,615,331 A | 10/1986 | Kramann |
| 4,654,092 A | 3/1987 | Melton |
| 4,655,771 A | 4/1987 | Wallsten |
| 4,657,024 A | 4/1987 | Coneys |
| 4,681,110 A | 7/1987 | Wiktor |
| 4,692,139 A | 9/1987 | Stiles |
| 4,697,595 A | 10/1987 | Breyer et al. |
| 4,698,058 A | 10/1987 | Greenfeld et al. |
| 4,706,681 A | 11/1987 | Breyer et al. |
| 4,719,916 A | 1/1988 | Ravo |
| 4,724,846 A | 2/1988 | Evans, III |
| 4,731,084 A | 3/1988 | Dunn et al. |
| 4,732,152 A | 3/1988 | Wallsten |
| 4,733,665 A | 3/1988 | Palmaz |
| 4,748,971 A | 6/1988 | Borodulin et al. |
| 4,748,986 A | 6/1988 | Morrison et al. |
| 4,750,488 A | 6/1988 | Wuchinich et al. |
| 4,750,902 A | 6/1988 | Wuchinich et al. |
| 4,751,916 A | 6/1988 | Bory |
| 4,760,849 A | 8/1988 | Kropf |
| 4,768,507 A | 9/1988 | Fischell et al. |
| 4,770,664 A | 9/1988 | Gogolewski |
| 4,771,773 A | 9/1988 | Kropf |
| 4,793,348 A | 12/1988 | Palmaz |
| 4,796,637 A | 1/1989 | Mascuch et al. |
| 4,800,890 A | 1/1989 | Cramer |
| 4,808,246 A | 2/1989 | Albrecht et al. |
| 4,816,018 A | 3/1989 | Parisi |
| 4,817,600 A | 4/1989 | Herms et al. |
| 4,819,618 A | 4/1989 | Liprie |
| 4,823,793 A | 4/1989 | Angulo et al. |
| 4,830,003 A | 5/1989 | Wolff et al. |
| 4,830,023 A | 5/1989 | de Toledo et al. |
| 4,830,262 A | 5/1989 | Ishibe |
| 4,834,747 A | 5/1989 | Gogolewski |
| 4,842,590 A | 6/1989 | Tanabe et al. |
| 4,846,186 A | 7/1989 | Box et al. |
| 4,848,343 A | 7/1989 | Wallsten |
| 4,848,348 A | 7/1989 | Craighead |
| 4,850,999 A | 7/1989 | Planck |
| 4,856,516 A | 8/1989 | Hillstead |
| 4,867,173 A | 9/1989 | Leoni |
| 4,870,953 A | 10/1989 | DonMichael et al. |
| 4,875,480 A | 10/1989 | Imbert |
| 4,883,486 A | 11/1989 | Kapadia et al. |
| 4,884,579 A | 12/1989 | Engelson |
| 4,886,062 A | 12/1989 | Wiktor |
| 4,899,733 A | 2/1990 | DeCastro et al. |
| 4,906,241 A | 3/1990 | Noddin |
| 4,907,572 A | 3/1990 | Borodulin et al. |
| 4,920,954 A | 5/1990 | Alliger et al. |
| 4,922,905 A | 5/1990 | Strecker |
| 4,922,924 A | 5/1990 | Gambale et al. |
| 4,925,445 A | 5/1990 | Sakamoto et al. |
| 4,932,419 A | 6/1990 | de Toledo |
| 4,934,380 A | 6/1990 | de Toledo |
| 4,936,845 A | 6/1990 | Stevens |
| 4,950,227 A * | 8/1990 | Savin et al. .................... 604/8 |
| 4,953,553 A | 9/1990 | Tremulis |
| 4,954,126 A | 9/1990 | Wallsten |
| 4,957,110 A | 9/1990 | Vogel et al. |
| 4,964,409 A | 10/1990 | Tremulis |
| 4,969,891 A * | 11/1990 | Gewertz .................... 606/200 |
| 4,971,490 A | 11/1990 | Hawkins |
| 4,980,964 A | 1/1991 | Boeke |
| 4,984,581 A | 1/1991 | Stice |
| 4,989,608 A | 2/1991 | Ratner |
| 4,990,151 A | 2/1991 | Wallsten |
| 4,991,602 A | 2/1991 | Amplatz et al. ............ 128/772 |
| 4,995,878 A | 2/1991 | Rai |
| 5,001,825 A | 3/1991 | Halpern |
| 5,003,987 A | 4/1991 | Grinwald |
| 5,003,989 A | 4/1991 | Taylor |
| 5,012,797 A | 5/1991 | Liang et al. |
| 5,015,183 A | 5/1991 | Fenick |
| 5,015,253 A | 5/1991 | MacGregor |
| 5,019,085 A | 5/1991 | Hillstead |
| 5,019,090 A | 5/1991 | Pinchuk |
| 5,024,232 A | 6/1991 | Smid et al. |
| 5,024,617 A | 6/1991 | Karpiel |
| 5,025,799 A | 6/1991 | Wilson |
| 5,026,377 A | 6/1991 | Burton et al. |
| 5,040,283 A | 8/1991 | Pelgrom |
| 5,046,428 A * | 9/1991 | Cope et al. .................. 606/127 |
| 5,047,050 A | 9/1991 | Arpesani |
| 5,052,407 A | 10/1991 | Hauser et al. |
| 5,059,166 A | 10/1991 | Fischell et al. |
| 5,061,275 A | 10/1991 | Wallsten et al. |
| 5,064,435 A | 11/1991 | Porter |
| 5,069,217 A | 12/1991 | Fleischacker, Jr. |
| 5,069,226 A | 12/1991 | Yamauchi et al. .......... 128/772 |
| 5,071,407 A | 12/1991 | Termin et al. |
| 5,092,877 A | 3/1992 | Pinchuk |
| 5,095,915 A | 3/1992 | Engelson |
| 5,104,404 A | 4/1992 | Wolff |
| 5,109,830 A | 5/1992 | Cho |
| 5,111,829 A | 5/1992 | de Toledo |
| 5,129,890 A | 7/1992 | Bates et al. |
| 5,139,480 A | 8/1992 | Hickle et al. |

| | | | |
|---|---|---|---|
| 5,147,317 A | * 9/1992 | Shark et al. ............... 604/164 |
| 5,147,385 A | 9/1992 | Beck et al. |
| 5,152,777 A | * 10/1992 | Goldberg et al. .......... 606/200 |
| 5,163,433 A | 11/1992 | Kagawa et al. |
| 5,163,952 A | 11/1992 | Froix |
| 5,171,233 A | 12/1992 | Amplatz |
| 5,171,262 A | 12/1992 | MacGregor |
| 5,176,617 A | 1/1993 | Fischell et al. |
| 5,197,978 A | 3/1993 | Hess |
| 5,201,901 A | 4/1993 | Harada et al. |
| 5,207,706 A | 5/1993 | Menaker |
| 5,213,111 A | 5/1993 | Cook et al. |
| 5,217,483 A | 6/1993 | Tower |
| 5,256,158 A | 10/1993 | Tolkoff et al. |
| 5,256,764 A | 10/1993 | Tang et al. |
| 5,276,455 A | 1/1994 | Fitzsimmons et al. |
| 5,304,140 A | 4/1994 | Kugo et al. |
| 5,320,100 A | 6/1994 | Herweck et al. |
| 5,334,201 A | 8/1994 | Cowan |
| 5,354,309 A | 10/1994 | Schnepp-Pesch et al. |
| 5,360,442 A | 11/1994 | Dahl et al. |
| 5,366,504 A | 11/1994 | Anderson et al. |
| 5,368,661 A | 11/1994 | Nakamura et al. |
| 5,374,261 A | 12/1994 | Yoon |
| 5,382,259 A | 1/1995 | Phelps et al. |
| 5,389,106 A | 2/1995 | Tower |
| 5,474,563 A | 12/1995 | Myler et al. |
| 5,476,508 A | 12/1995 | Amstrup |
| 5,489,277 A | 2/1996 | Tolkoff et al. |
| 5,496,330 A | * 3/1996 | Bates et al. ............... 606/127 |
| 5,498,236 A | 3/1996 | Dubrul et al. |
| 5,514,154 A | 5/1996 | Lau et al. |
| 5,531,788 A | 7/1996 | Dibie et al. ............... 623/11 |
| 5,556,413 A | 9/1996 | Lau et al. |
| 5,609,629 A | 3/1997 | Fearnot et al. |
| 5,628,787 A | 5/1997 | Mayer |
| 5,630,840 A | 5/1997 | Mayer |
| 5,658,296 A | * 8/1997 | Bates et al. ............... 606/127 |
| 5,725,549 A | 3/1998 | Lam |
| 5,725,570 A | 3/1998 | Heath |
| 5,733,326 A | 3/1998 | Tomonto et al. |
| 5,843,163 A | 12/1998 | Wall |
| 5,858,556 A | 1/1999 | Eckert et al. |
| 5,879,382 A | 3/1999 | Boneau |
| 5,902,332 A | 5/1999 | Schatz |

FOREIGN PATENT DOCUMENTS

| | | |
|---|---|---|
| EP | 0 405 823 A2 | 1/1991 |
| EP | 0 433 011 | 6/1991 |
| EP | 0 435 518 | 7/1991 |
| EP | 0 042 703 A1 | 12/1991 |
| EP | 0 481 365 | 4/1992 |
| EP | 0 547 739 | 6/1993 |
| EP | 0 556 940 A1 | 8/1993 |
| EP | 0 593 163 A1 | 4/1994 |
| FR | 2 479 685 | 3/1981 |
| GB | 1 205 743 | 9/1970 |
| GB | 2 195 257 | 4/1988 |
| JP | 53-19958 | 7/1976 |
| JP | 59-29958 | 11/1978 |
| JP | 1-259541 | 10/1989 |
| WO | WO 88/01924 | 3/1988 |
| WO | WO 90/01300 | 2/1990 |
| WO | WO 91/04716 | 4/1991 |
| WO | WO 91/19528 | 12/1991 |
| WO | WO 92/11815 | 7/1992 |
| WO | WO 92/13483 | 8/1992 |
| WO | WO 92/19310 | 11/1992 |
| WO | WO 92/21399 | 12/1992 |
| WO | WO 93/19803 | 10/1993 |
| WO | WO 93/19804 | 10/1993 |
| WO | WO 94/16646 | 8/1994 |
| WO | WO 94/24961 | 11/1994 |
| WO | WO 97/04895 | 2/1997 |

OTHER PUBLICATIONS

Alliger et al., "Tumorichidal Effect of a New Ultrasonic Needle", Federation Proceedings—Abstracts, vol. 44, No. 4, Mar. 5, 1985, p. 1145.

Ariani et al., "Dissolution of Peripheral Arterial Thrombi by Ultrasound", Circulation (American Heart Association), vol. 84, No. 4, Oct. 1991, pp. 1680–1688.

Chae et al., "Ultrasonic Dissolution of Human Thrombi", Journal of the American College of Cardiology, vol. 15, No. 7, Jun. 1990, p. 64A.

Chaussy et al., "Transurethral Ultransonic Ureterolithotripsy Using a Solid–Wire Probe", Urology, vol. XXIX, No. 5, May 1987, pp. 531–532.

Chaussy et al., "Transurethral Ultrasonic Uretero–Lithotripsy: A New Technique", The Journal of Radiology, vol. 137, No. 4, Part 2, Apr. 1987, p. 159A.

Demer et al., "High Intensity Ultrasound Increases Distensibility of Calcific Atherosclerotic Arteries", Journal of the American College of Cardiology, vol. 18, No. 5, Nov. 1, 1991, pp. 1259–1262.

Ernst et al., "Ability of High–Intensity Ultrasound to Ablate Human Atherosclerotic Plaques and Minimize Debris Size", The American Journal of Cardiology, vol. 68, No. 2, Jul. 15, 1991, pp. 242–246.

Freeman et al., "Ultrasonic Angioplasty Using a New Flexible Wire System", Journal of the American College of Cardiology, vol. 13, No. 1, Jan. 189, p. 4A.

Freeman et al., "Ultrasonic Energy Produces Edothelium–Dependent Vasomotor Relaxation in Vitro", Clinical Research–Official Publication of the Amer. Federation for Clin. Research, vol. 36, No. 5, Sep. 1988, p. 786A.

Goodfriend, "Ultrasonic Ureterolithotripsy Employed in a Flexible Ureteroscope", The Journal of Urology, vol. 139, No. 4, Part 2, Apr. 1988, p. 282A.

Goodfriend, "Ultrasonic and Electrohydraulic Lithotripsy of Ureteral Calculi", Urology, vol. XXIII, No. 1, Jan. 1984, pp. 5–8.

Goodfriend, "Transvesical Intussusception Ureterectomy", vol. XXI, No. 4, Apr. 1983, pp. 414–415.

Goodfriend, "Disintegration of Ureteral Calculi by Ultrasound", Urology, vol. 1, No. 3, Mar. 1973, pp. 260–263.

Hong et al., "Ultrasonic clot disruption: An in vitro study", American Heart Journal, vol. 20, No. 2, Aug. 1990, pp. 418–422.

Hunter et al., "Transurethral Ultrasonic: Uretero–lithotripsy", The Journal of Urology, vol. 135, No. 4, Part 2, Apr. 1986, p. 299A.

Marco et al., "Intracoronary Ultra Sound Imaging: Preliminary Clinical Results", European Heart Journal–Journal of the European Society of Cardiology–Abstract Supplement (Academic Press), Aug. 1990, p. 190.

Monteverde et al., "Ultrasound Arterial Recanalization in Acute Myocardial Infarction", Supplement to Circulation (American Heart Association), vol. 82, No. 4, Oct. 1990, pp. III–622.

Monteverde et al., "Percutaneous Transluminal Ultrasonic Angioplasty in Totally Occluded Peripheral Arteries: Imm.&Intermed.Clinical Results", Suppl. to Circ. (Am. Hrt. Assoc.), 82:4, Oct. 1990, pp. III–678.

Rosenschein et al., "Clinical Experience with Ultrasonic Angioplasty of Totally Occluded Peripheral Arteries", Journal of the Am. College of Cardiology, vol. 15, No. 1, Jan. 1990, p. 104A.

Siegel et al., "In Vivo Ultrasound Arterial Recanalization of Atherosclerotic Total Occlusions", Journ. of the American College of Cardiology, vol. 15, No. 2, Feb. 1990, pp. 345–351.

Siegel et al., "Percutaneous Ultrasonic Angioplasty: Initial Clinical Experience", The Lancet, vol. II, No. 8666, Sep. 30, 1989, pp. 772–774.

Siegel et al., "Ultrasonic Plaque Ablation—A New Method for Recanalization of Partially or Totally Occluded Arteries", Circulation, vol. 78, No. 6, Dec. 1988, pp. 1443–1448.

Katzen™ Infusion Wire, "the first multi–sidehole infusion wire designed from thrombolysis", Medi–tech.

*DFT Drawn Filled Tubing (1988).

*ASTM Standards 1991 Annual Book, vol. 13.01 Medical Devices.

* cited by examiner

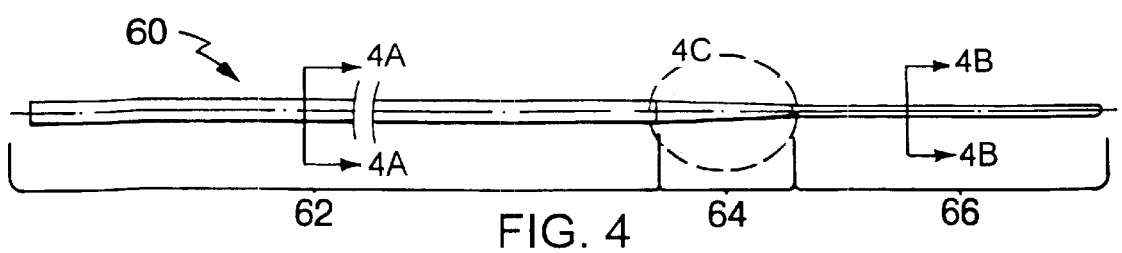
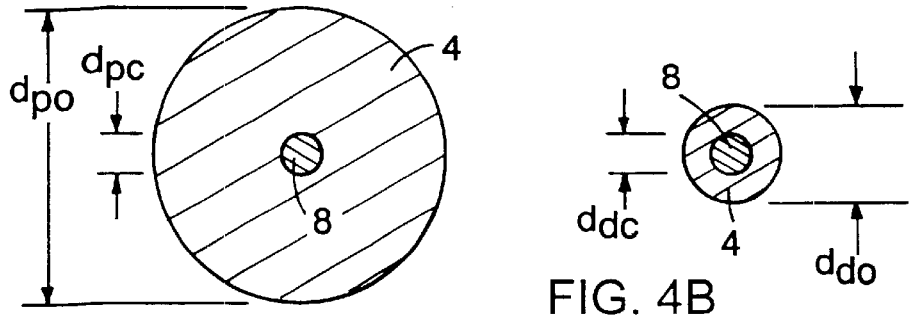
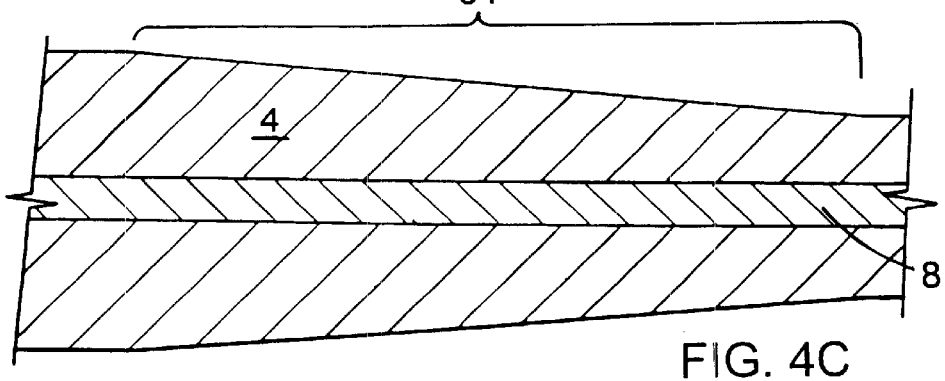
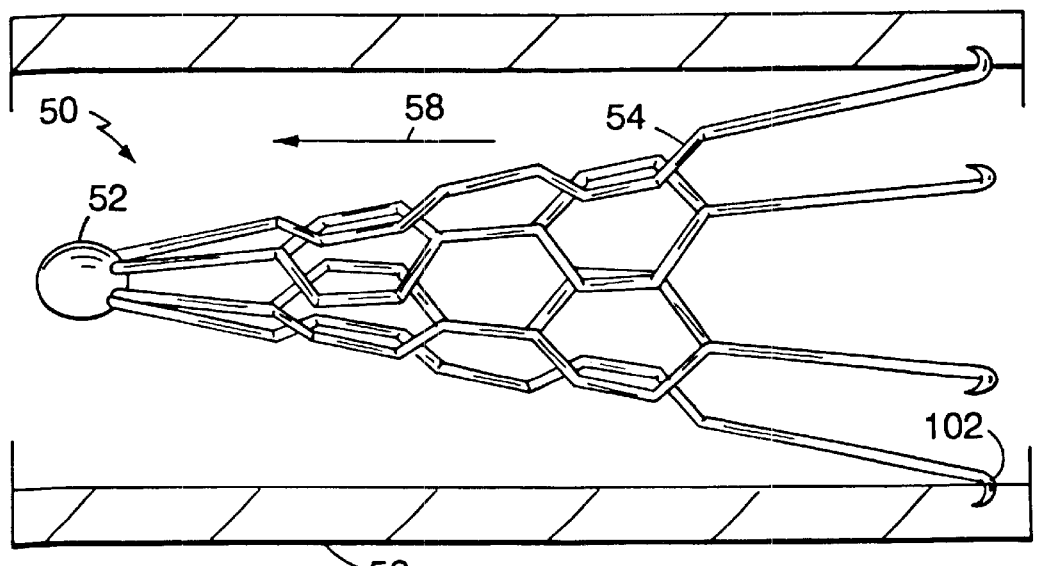

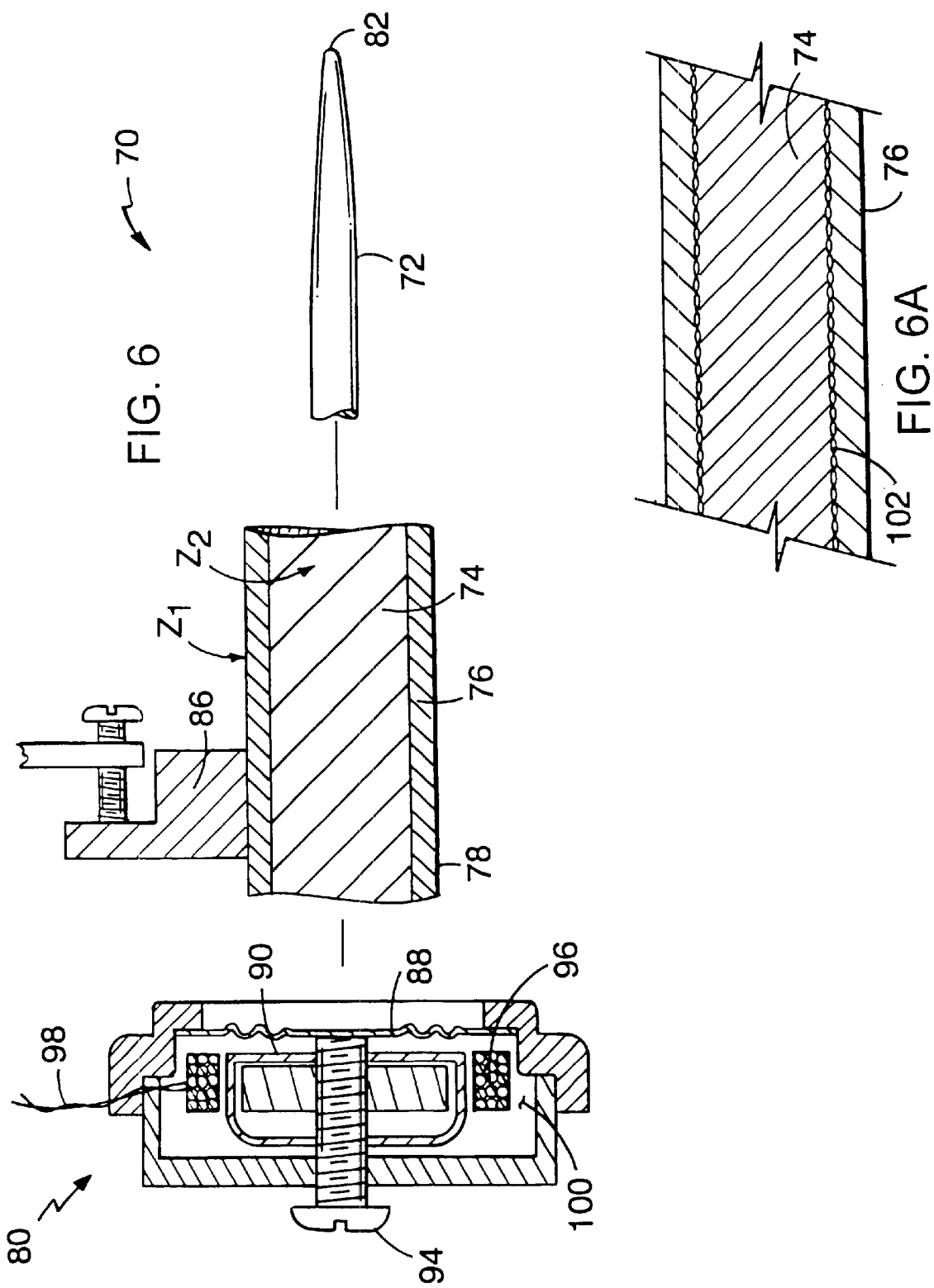

METAL MEDICAL DEVICE

This is a continuation of U.S. Ser. No. 08/756,187 filed Nov. 25, 1996 now abandoned which is a continuation of U.S. Ser. No. 08/527,749 filed Sep. 13, 1995 now abandoned which is a continuation of U.S. Ser. No. 07/861,253, filed Mar. 31, 1992 now abandoned, which is incorporated herein by reference.

FIELD OF THE INVENTION

This invention relates to metal medical components to be used inside the body.

BACKGROUND OF THE INVENTION

Noninvasive medical procedures reduce the risk of surgery by introducing medical devices to a body cavity through small incisions or body orifices. The devices are carefully designed so that they may be controlled from the proximal end remaining outside the body to carry out the required treatment at the desired location inside the body. In one of the most common noninvasive techniques, angiography, a device, such as a guidewire, balloon angioplasty catheter or the like, is advanced and torqued at its proximal end to steer the device through a blood vessel to the position of an occlusion at which point a medical procedure such as balloon angioplasty and/or positioning of an endoprosthesis is carried out.

Typically, X-ray fluoroscopy is used to view the medical device within the body cavity to monitor placement and operation. The device may also be viewed by X-ray film after placement. To use these techniques, particularly with small devices which may be difficult to view, the medical device must include some radiopaque material, more dense than the surrounding tissue, to provide sufficient contrast on an X-ray image. A highly dense, and therefore particularly radiopaque, metal is usually incorporated with the portion of the medical device used inside the body for this purpose.

SUMMARY OF THE INVENTION

In interventional medicine, wires can be used for a variety of purposes such as tracking, stenting, filtering, conducting (electric current, ultrasound energy, etc.) and marking. Desirable attributes of these wires vary with application, but include properties such as stiffness, tensile strength, elasticity, radiopacity, weldability, flexural life, conductivity, etc. These properties are hard to find in single-material constructions. It is possible to achieve optimum properties by creating a multiple material coaxial construction. In medical wires, for example, it can be very desirable to have high radiopacity along with elasticity and strength. This may be accomplished by combining a radiopaque material with an elastic material. Although it is possible to put either material on the inside or outside, it would be preferable to put the dense radiopaque material (e.g., tantalum) on the inside (core) since dense materials are generally less elastic and the elastic material (e.g., titanium or nickel-titanium alloy) on the outside (clad). The clad or "skin" of the wire will undergo more deformation in bending than the core, so the elastic component is best positioned at the skin. In another medical application, it is desirable to have an elastic core (nitinol) for conducting axial vibrations (sonic or ultrasonic) and a thin stiff cladding (stainless steel) in order to minimize traverse vibrations which result in loss of energy.

An aspect of the invention is a metal medical device with at least a portion to be used within the body with properties that can be tailored to a particular application. The portion is formed of preferably two or more dissimilar metals joined together to form a unitary member. Typically, each metal contributes a desirable property to the device which is not substantially impaired by the presence of the other metal. In particularly preferred devices, one metal provides enhanced radiopacity. In these embodiments, the medical device comprises a metal outer member having a predetermined density and an exposed outer surface and a core including a metal having a density greater than the outer member to enhance radiopacity. The core is secured within and substantially enclosed by the outer member. Preferably, the medical component is in the form of a wire configured such that the mechanical properties, for example, the elastic properties, of the metal forming the outer member are affected by the core to a desired degree so that the wire has a desired overall performance suitable for its intended use. Preferably, the mechanical properties of the outer longitudinal member dominate the properties of the wire yet the radiopacity is substantially enhanced by the denser core. The invention also allows increased radiopacity of a metal medical device without adversely affecting and in some cases improving other important properties such as the biocompatibility, size or other performance characteristics. These performance advantages can be realized by proper selection of the material of the outer member and core, their relative size, and geometrical configuration. The performance characteristics of the component may be dictated by the medical device into which the radiopaque medical component is to be incorporated.

The term "metal" as used herein includes electropositive chemical elements characterized by ductility, malleability, luster, and conductivity of heat and electricity, which can replace the hydrogen of an acid and forms bases with the hydroxyl radical and including mixtures including these elements and alloys. Many examples are given below.

In one aspect, the invention features a medical device having at least a portion for use within the body. The portion includes an extended metal outer member having an exposed outer surface and a core within the outer member formed of a metal different than the metal of the outer member. The core is secured within and substantially enclosed by the outer member.

Various preferred embodiments may include one or more of the following features. The extended metal outer member is comprised of a metal of predetermined density and the core is comprised of a metal having a density substantially greater than the outer member to enhance radiopacity of the device. The portion is in the form of a medical wire, wherein the metal outer member is a longitudinal member and the radiopaque core is positioned along the axis of the longitudinal member. The radiopaque core has a density of about 9.9 g/cc or greater. The core is selected from the group consisting of tungsten, tantalum, rhenium, iridium, silver, gold, bismuth, platinum and alloys thereof. The core has a modulus of elasticity of about 550 GPa or less. The core has a modulus of elasticity of about 200 GPa or less. The outer member is selected from the group consisting of superelastic alloys, precursor alloys of superelastic alloys, stainless steel, and titanium and its alloys.

The superelastical alloy is nitinol. The core is about 1 to 40% of the cross-sectional dimension of the component. The core is about 25% or more of the cross-sectional dimension of the component. The core is about 28% or less of the cross-sectional dimension of the component. The cross-sectional dimension of the component is less than about 0.025 inch. The outer member has a cross-section of about 0.0045 to 0.008 inch and the core member has a cross-section of about 0.0014 to 0.00195 inch inner diameter. The core is a solid metallic member. The outer member has portions of varying dimension. The outer member has a taper portion. The core has a constant inner dimension in portions corresponding to the varying outer dimension of the outer member. The portion is in the form of a medical guidewire. The portion is in the form of elastic leg members of a vascular filter. The outer member and core are of circular cross-sectional configuration. The portion is in the form of an ultrasonic probe. The probe is an elastic probe having a titanium core and nitinol outer member. The probe and core are constructed of materials of substantially different acoustic impedance. The acoustic energy is provided by axial excitation.

In another aspect, the invention features a medical wire device having at least a portion for use within the body. The portion includes an extended longitudinal metal outer member having a predetermined density and an exposed outer surface and a continuous solid core positioned along the axis of the outer member including a metal having a density of about 9.9 g/cc or greater and greater than the density of the outer member for enhancing radiopacity of the wire. The core is secured within and substantially enclosed by the outer member and is about 10 to 50% of the cross-sectional dimension of the portion for use within the body.

In various preferred embodiments, the core material is tantalum, the outer material is nitinol, and the cross-sectional dimension of the portion is about 0.025 inch or less. The outer member has a cross-section of about 0.0045 to 0.008 inch and the core member has a cross-section of about 0.0014 to 0.00195 inch inner diameter. The wire is in the form of a guidewire. The outer member has portions of varying dimension such as a taper portion. The core has a constant inner dimension in portions corresponding to the varying outer dimension of the outer member. The cross-sectional dimension of the portion is about 0.035 to 0.037 inch. The core is about 0.005 inch in diameter. The component is in the form of elastic leg members of a vascular filter.

In another aspect, the invention features a method for medical treatment by providing a medical device for performing a desired treatment, incorporating on at least a portion of the device a radiopaque medical component, formed of a metal outer member having a predetermined density and exposed outer surface and a core including a metal having a density substantially greater than the outer member to enhance radiopacity, the core being secured within and substantially enclosed by the outer member, and introducing the portion including the radiopaque medical component into the body, and observing the medical component by x-ray fluoroscopy.

In various preferred embodiments, the medical device is a guidewire and the medical component is a portion of the guidewire, the method further including steering the guidewire through the body from the proximal end. The medical device is a vascular filter.

In another aspect, the invention features a medical device capable of placement or manipulation in the body by means external of the body under guidance of a fluoroscope. The device is formed at least in part of an elongated wire-form metal member adapted to be subjected to elastic deformation to enable the device to be forced into a characteristic deformed configuration during a stage of use and to elastically self-recover from the deformation when deformation forces are relieved. The wire-form metal member is formed of a core of a first metal of a first selected thickness and an intimately surrounding sheath of a second selected metal of a second thickness, the first metal being a high density metal that demonstrates characteristic relatively high radiopacity and the second metal being a lower density metal having substantially more elasticity than the first metal, the combined effect of the selected thicknesses of the first and second metals in the wire-form member serving to enhance the radio-opacity of the wire-form member to provide improved fluoroscopic or x-ray visualization of the wire-form member in the body while imparting sufficient elasticity to enable the wire-form member to elastically self-recover from its characteristic deformed configuration.

In various preferred embodiments, the wire-form metal member comprises a draw-form. The second metal is nitinol. The high density metal is tantalum. The wire-form member comprises the main body of a medical guidewire.

DESCRIPTION OF THE PREFERRED EMBODIMENT(S) WE FIRST BRIEFLY DESCRIBE THE DRAWINGS.

DRAWINGS

FIG. 1 is a longitudinal cross-sectional view of a medical wire according to the invention; while

FIG. 4 is a view of a guidewire of the invention for introduction into a body lumen; while FIG. 4a a cross-sectional view along lines bb, FIG. 4b is a cross-sectional view along lines cc in FIG. 4; and FIG. 4c is a greatly enlarged cross-sectional view of portion d of FIG. 4;

FIG. 5 is a schematic of a blood clot filtration device of the invention for implantation in a blood vessel;

FIG. 6 is a schematic illustration of an ultrasonic wire device of the invention and FIG. 6a is longitudinal cross-sectional view of a portion of another embodiment of an ultrasonic device, having air-filled microspheres (shown greatly enlarged) at the interface of the core and outer member.

DESCRIPTION

Figure 1:
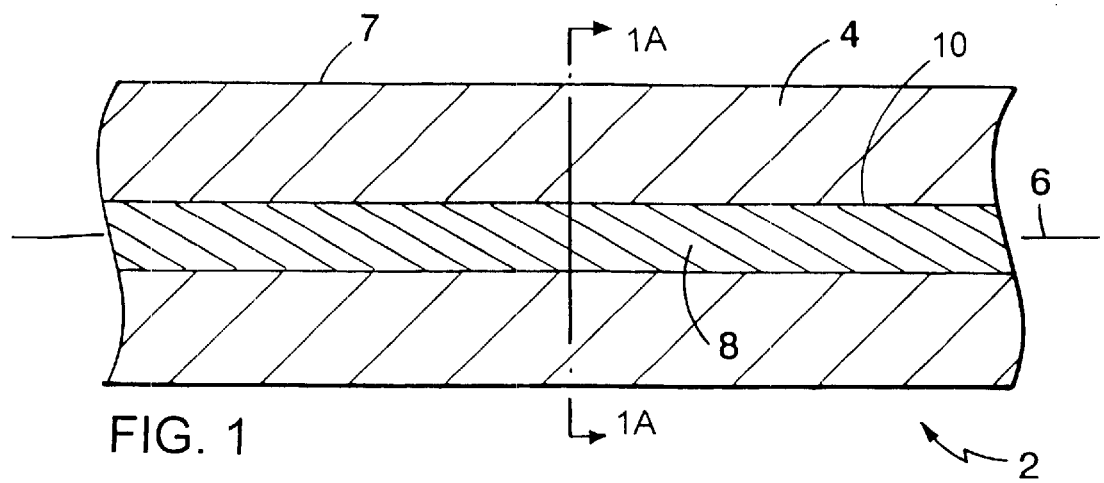
Figure 1A:
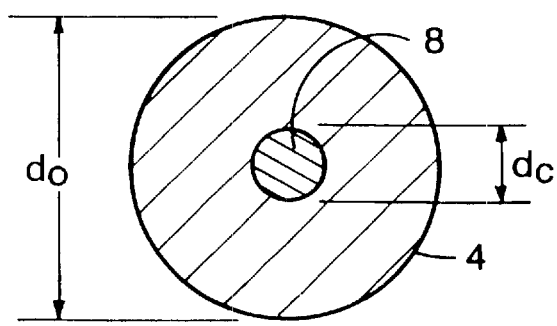
FIG. 1a is a cross-sectional view taken along the lines aa in FIG. 1.

Referring to FIGS. 1 and 1a, a preferred embodiment of the invention is a medical wire 2 that includes a longitudinal outer member 4 with an axis 6. The longitudinal member 4 is formed of a metal having desirable properties, such as high elasticity and biocompatibility of its exposed outer surface 7. (The surface 7 may include a non-metal coating of, e.g., fluorocarbons, silicones, hydrophilic and lubricous biocompatible materials.) About the axis 6 is a core material 8 including a metal with a density greater than the longitudinal member 4 to enhance the radiopacity of the wire. The core 8 is bonded to and substantially enclosed by the outer member 4 such that it does not have any substantial exposed surface and therefore does not contact body tissue when positioned within the body during use.

As illustrated, preferably the core 8 is a continuous solid member in intimate contact and bonded with the outer member 4 without the formation of substantial voids in the interface 10 between the core and outer member.

Preferably, the elastic properties of the wire 2 are dominated by the elastic properties of the longitudinal member 4. The core material 8 enhances the radiopacity of the wire 2 but preferably does not substantially effect the mechanical performance of the wire. In preferred embodiments, the cross-sectional dimension of the core ($d_c$) is less than about 70% (but typically greater than about 1% or 10%) of the outer cross-sectional dimension ($d_o$) of the wire, more preferably between about 40% and 25%. The wire is especially useful in applications where the medical device must be sized small, such as for use in the vascular system, for example, as a guidewire tip which has an outer dimension ($d_o$) of less than about 0.015 inch, e.g., even less than 0.0075 inch and for which less dense metals are required for advantageous elastic properties. The invention is particularly useful for enhancing radiopacity of devices with dimensions of about 0.025 inch or less.

Figure 2:
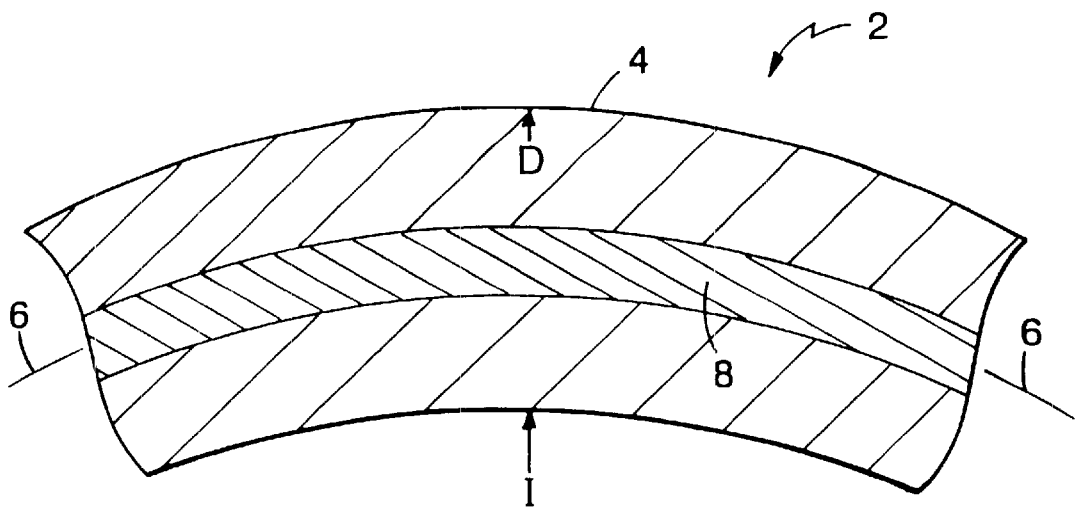
FIG. 2 is a schematic illustration of a wire according to the invention in a stressed, bent configuration.

Referring to FIG. 2, the wire 2 is shown in a bent position, as it may be, for example when in use in a device positioned within the body. The inner and outer portions (i) and (o), experience a wide range of tension and compression as the wire is bent. An advantage of the invention, is that by positioning the core material 8 near the axis 6, the range of tension and compression imposed on the core is reduced and a wide latitude of dense, substantially radiopaque materials can be used which would otherwise might not be suitable for their response to bending or other mechanical properties.

The relative dimension of the core and outer member and the particular materials used for these elements are selected based on the desired over-all mechanical properties of the wire and the degree to which x-ray visibility is to be enhanced, since the core affects the mechanical properties of the wire compared to a solid wire formed of the outer material, and the radiopacity is a function of the sum of the mass between an x-ray beam source and detector. For example, large devices or devices with overlapping portions, may require less radiopaque material to provide sufficient visibility. Similarly, the location of use in the body may affect the amount of dense material needed for sufficient visibility. The visibility of a device can be tested by known techniques such as ASTM Designation F640–79 "Standard Test Method for Radiopacity of Plastics for Medical Use". In this test, the background densities which may be encountered clinically are mimicked by an aluminum plate positioned over the wire having various thicknesses.

The properties of the outer member metal and core which may be considered include density, modulus of elasticity (in annealed and hardened states), biocompatability (primarily a factor for the material of the outer longitudinal member), flexural stiffness, durability, tensile and compression strength, acoustic impedance (as discussed in a further embodiment below) and the required radiopacity and resolution.

Preferably, for elastic members, the outer member is formed of a continuous solid mass of a highly elastic biocompatible metal such as a superelastic or pseudo-elastic metal alloy, for example, a nitinol (e.g., 55% nickel, 45% titanium). Other examples of superelastic materials include, e.g., Silver-Cadmium (Ag—Cd), Gold-Cadmium (Au—Cd), Gold-Copper-Zinc (Au—Cu—Zn), Copper-Aluminum-Nickel (Cu—Al—Ni), Copper-Gold-Zinc (Cu—Au—Zn), Copper-Zinc (Cu—Zn), Copper-Zinc-aluminum (Cu—Zn—Al), Copper-Zinc-Tin (Cu—Zn—Sn), Copper-Zinc-Xenon (Cu—Zn—Xe), Iron Beryllium ($Fe_3Be$), Iron Platinum ($Fe_3Pt$), Indium-Thallium (In—Tl), iron-manganese (Fe—Mn) Nickel-Titanium-Vanadium (Ni—Ti—V), Iron-Nickel-Titanium-Cobalt (Fe—Ni—Ti—Co) and Copper-Tin (Cu—Sn). See Schetsky, L. McDonald, "Shape Memory Alloys", *Encyclopedia of Chemical Technology* (3rd ed.), John Wiley & Sons, 1982, vol. 20. pp. 726–736 for a full discussion of superelastic alloys. Other examples of metals suitable for the outer member include stainless steel, titanium and various alloys of these metals and the precursor of superelastic alloys. Precursors of superelastic alloys are those alloys which have the same chemical constituents as superelastic alloys, but have not been processed to impart the superelastic property. Such alloys are further described in co-owned and co-pending U.S. Ser. No. 07/507,375, filed Apr. 10, 1990, the entire contents of which is hereby incorporated by reference.

The core material is preferably a continuous solid mass, but may also be in a powder-form. The core includes a metal that is relatively dense to enhance radiopacity. Preferably, the core metal has a density of about 9.9 g/cc or greater. Most preferably, the core is formed of tantalum (density =16.6 g/cc). Other preferred materials and their density include tungsten (19.3 g/cc), rhenium (21.2 g/cc), bismuth (9.9 g/cc), silver (16.49 g/cc), gold (19.3 g/cc), platinum (21.45 g/cc), and iridium (22.4 g/cc). In some cases barium can be used in the core. The core may be formed of alloys such as those including the above materials. Typically, the core is somewhat stiffer than the outer membrane. Preferably, the core metal has a low modulus of elasticity, e.g., preferably below about 550 GPa, e.g., such as tantalum (186 GPa). A smaller difference between the modulus of elasticity between the outer material and core, results in a smaller variation of the modulus from that of the outer material in the wire of the invention. For larger differences, a smaller core may be used so as to produce a wire in which the elastic properties are dominated by the outer material.

The outer member and core may be in many cross-sectional geometric configurations, such as circular, square, triangular, hexagonal, octagonal, trapezoidal and the geometrical configuration of the core may differ from that of the longitudinal member. For example, the wire may be rectangular in cross-section with a rectangular core or triangular or hexagonal in cross-section with a circular core. The wire may also take on the form of tubing with a lumen within the core extending along the axis of the wire. The wire may also include successive layers of different metals to form a composite system. The core may extend intermittently along the axis in a desired pattern.

The medical device may be formed, for example, by drilling a relatively large rod of the outer member material to form a lumen, positioning a rod of core material in the lumen, sealing the ends of the lumen, e.g., by crimping and drawing as known in the art, through a series of dies of decreasing diameter until the desired outer diameter is achieved. The device may be heat treated to anneal, harden or impart superelastic properties. Other methods of formation may be, e.g., by coating the core with the desired outer material such as by electro- or electroless plating. The materials used in the outer member and core are also selected based on their workability for forming the wire, including factors such as machinability, for forming the longitudinal member into a tubular piece and the core member into a rod shaped piece, stability in gaseous environments at annealing temperatures, properties related to welding, drawing, forging, swaging, the ability to accept coatings such as adhesives, polymers, lubricants and practical aspects such as cost and availability.

Other examples follow.

EXAMPLE 1

A 500 foot length of wire (0.0052 inch in diameter) having an outer member formed of a precursor of a nitinol (55% Ni/45% Ti) superelastic alloy and a core material of tantalum (0.00175 inch in diameter) is formed by drilling a 0.25 inch diameter bore in a 0.75 inch rod of the outer member material and providing in the drilled lumen a tantalum member of substantially matched outer diameter. The rod is mechanically forged in a standard hot forging and rolling apparatus, then hammered such that no substantial voids between the core and outer longitudinal member are present. One end of the rod is sealed and the opposite end is cold drawn longitudinally through a dye to the final diameter. Initially, the outer member of the wire is the precursor of a superelastic alloy, i.e., it has not been heat treated to impart the superelastic property.

Figure 3:
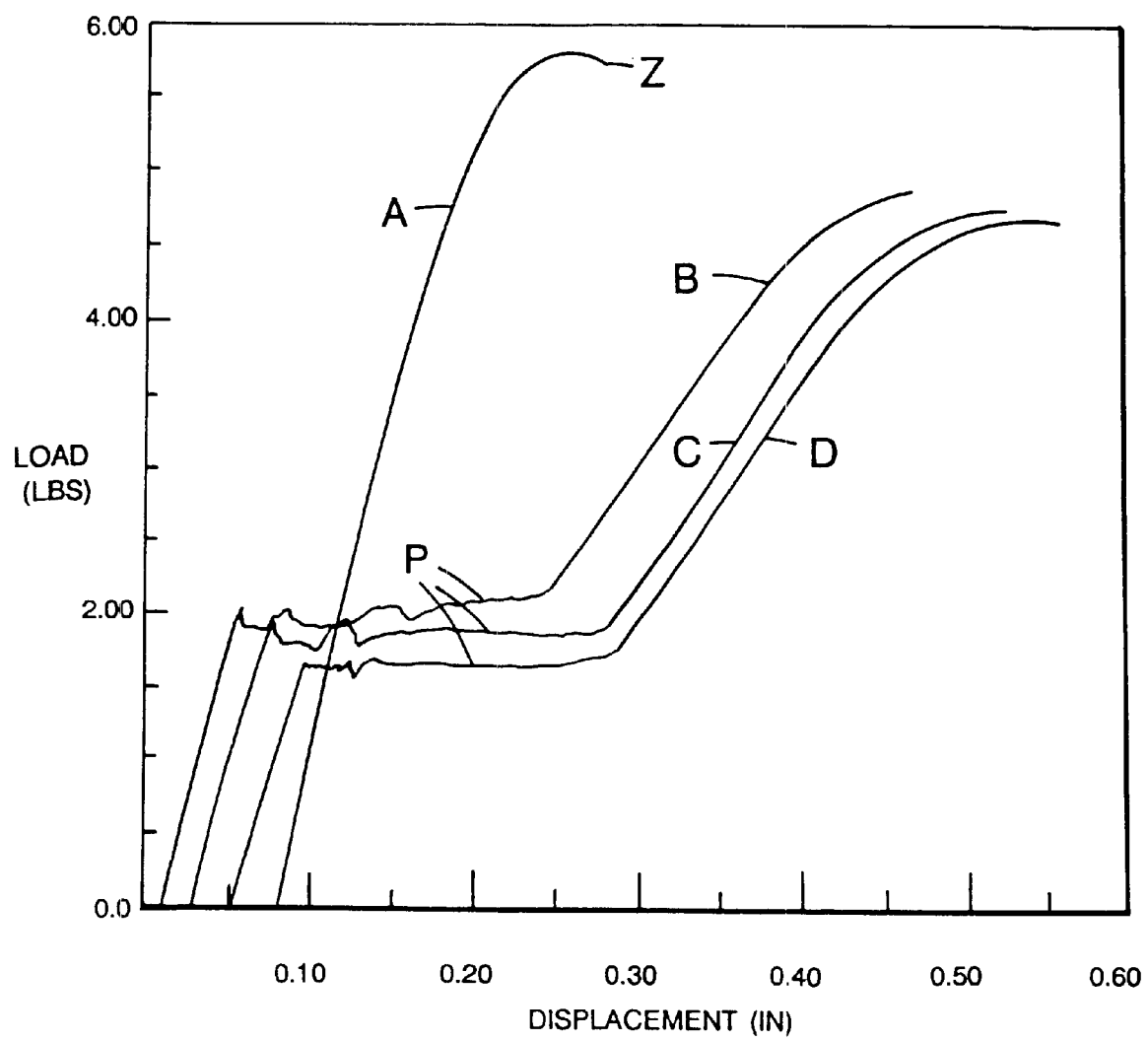
FIG. 3 is a graph of load versus displacement for several wires according to the invention.

Referring to FIG. 3, load versus displacement curves are illustrated. (For clarity, curves C, D and A are offset, successively, 0.025 inch on the x-axis.) Curve A illustrates the wire as discussed in the above paragraph prior to heat annealing which induces the superelastic property; the wire exhibits substantially linear elastic strain as a function of stress to a break point z. Curves B, C, D illustrate stress/strain curves after annealing the wire at 460° C. for 3 minutes, 5 minutes and 15 minutes, respectively. As these curves illustrate, the superelastic nature of the wire is substantially preserved, as evidenced by the substantial plateaus (p) on the stress/strain curve, despite the presence of the tantalum core. Also as illustrated, the stress at which constant displacement occurs decreases with increasing annealing, as would be expected with a superelastic material. The mechanical properties of the wire, therefore, are dominated by the nitinol alloy, despite the presence of the tantalum core.

Referring to Table I, the modulus of elasticity and plateau stress calculated based on stress-strain measurements as above, are compared for the wires of the invention and a solid wire of Ni—Ti alloy.

TABLE I

| | Ni—Ti | Ta Cored Ni—Ti | % Charge in Cored Wire |
|---|---|---|---|
| Diameter | .0038" | .0052" | — |
| Area (Modulus of Elasticity) | 1.134 × 10⁻⁵ in² | 2.124 × 10⁻⁵ in² | — |
| Precursor | 5,401,300 psi | 7,373,865 psi | +27% |
| 460° @ 3 mins | 6,967,150 psi | 6,657,000 psi | −4.5% |
| 460° @ 5 mins | 5,381,160 psi | 5,721,100 psi | +6.0% |
| 460° @ 10 mins | 5,139,310 psi | — | — |
| 460° @ 15 mins | 5,143,960 psi | 5,551,924 | +7.4% |
| Plateau Stress (loading) | | | |
| 460° @ 3 mins | 101,400 psi | 94,174 | −7.2% |
| 460° @ 5 mins | 89,056 psi | 84,757 | −4.8% |
| 460° @ 10 mins | 79,357 psi | — | — |
| 460° @ 15 mins | 72,303 psi | 75,339 psi | +4.1% |

As the results in Table I illustrate, the modulus of elasticity of the wires of the invention was varied less than 30% compared to the solid Ni—Ti wire. The plateau stress of the wires of the invention using a superelastic outer member was varied less than about 10% compared to a solid Ni—Ti superelastic wire. The wire formed as described exhibits about 30% or more enhanced x-ray visibility over a wire of the same thickness formed of solid material. Preferably, wires as described, dominated by the mechanical properties of the outer superelastic member and exhibiting generally satisfactory radiopacity have outer diameter ($d_o$) of about 0.008 to 0.0045 inch with a core diameter ($d_c$) of about 0.0014 to 0.00195 inch.

EXAMPLE 2

Referring now to FIG. 4, a guidewire is shown of the type introduced into the body lumen, e.g., a blood vessel for positioning, for example, a catheter or the like. The guidewire 60 includes a proximal body section 62 of constant diameter, a taper 64 and a distal end 66 of constant, smaller diameter than the body section 62. Referring to FIG. 4a, in the preferred embodiment, the outer diameter of the proximal end 62 is $d_{po}$ about 0.038 inch and the diameter of the core is, $d_{pc}$, about 0.003 inch. Referring to FIG. 4b, at the distal end 66, the outer diameter is $d_{do}$ about 0.005 to 0.008 inch and the core is $d_{dc}$ about 0.003 inch. In the taper 64, only the outer member 4 tapers to reduced diameter, while the core remains of constant diameter. Such a wire might be formed by preparing a specimen of the outer material with an inner lumen, drawing the outer material to form the taper and reduced diameter distal portion, followed by positioning the core in the lumen. Alternatively, the structure of FIGS. 4 et seq. could be formed from a wire of constant diameter outer member and core and removing portions of the outer member, e.g., by grinding, to leave a relatively lower ratio of outer member to core in the taper and distal end. Alternatively, the core may taper at the same position as the outer member tapers by drawing the wire to form the taper after positioning the core within the outer material. The radiopaque core preferably extends the length of the wire so that the entire wire can be imaged, allowing viewing of the length of a tortuous body lumen. The cored wire may also be used as the distal tip of a conventional wire. The guidewire may also include a coil spring, e.g., about the distal tapered region, and/or incorporate a polymer coating. As well as improving the radiopacity, the cored wire can be tailored to exhibit other advantageous features, such as enhanced tensile strength by using a core material that has this property.

EXAMPLE 3

Referring to FIG. 5, a wire of the invention may also be used in a blood clot filtration device of the type positioned within a blood vessel. The filtration device 50 includes a nose cone 52 downstream relative to blood flow 58 and a series of legs 54. The legs include hook members 102 which are embedded in the wall 56 of the body lumen to secure the filter therein. A filter of this type is further described in Herms U.S. Pat. No. 4,817,600 and El-Nou Nou U.S. Pat. No. 5,059,205, the entire contents of which are hereby incorporated by reference. The wires 54 are formed as described herein including a radiopaque core within an elastic longitudinal member. Preferably, the overall diameter of the wire is 0.035 to 0.037 with a core diameter of about 0.005 inch. The outer member is preferably nitinol, stainless steel or titanium and the core is tantalum. It will be understood that smaller diameter wires for smaller filtration device legs may also be used, in which case, a dense core is particularly useful for enhancing radiopacity.

EXAMPLE 4

Referring now to FIGS. 6 and 6a, an ultrasonic device 70 is shown to include a wire 72 including an inner core 74 and an outer member 76. The wire 72 extends from a proximal end 78, attached to an ultrasonic source mechanism 80, to a distal end 82 which is positioned at a location where ultrasonic energy is to be delivered. Briefly, the source 80 includes a clamping mechanism 86 to couple the core near the distal end 78 of the wire to a diaphragm 88 which is vibrated ultrasonically by a piston transducer 90. The transducer 90 includes a phosphorous-bronze bell 92 whose tension may be adjusted by screw member 94. The magnetic field from coils 96 cause the transducer to vibrate when electrical energy is supplied through leads 98. Cooling vents 100 surround the coils 98. Ultrasonic energy supplied by the mechanism 80 to the core at the proximal portion 78 of the wire is transmitted through the core to the distal end 82 where it can be utilized to treat tissue. Referring to FIG. 6a, in some embodiments, the core 74 is bonded to the outer member 76 at intermittent points, leaving therebetween air-filled microspheres 102 which impede the transmission of ultrasonic energy laterally. The microspheres could be produced by machining grooves into the core or outer member before assembly.

By proper selection of the outer and core metals enhanced transmission of ultrasonic energy through the core may be achieved while minimizing lateral mode losses through the outer material. Preferably, the metals are selected based on their acoustic impedance ($Z_1$, $Z_2$) to induce internal reflection of acoustic waves propagating off axis. An advantage of the system is that lower power may be applied so that the transmission system operates at lower temperature. The outer member can further be selected to reduce vibration. A preferred embodiment of an elastic probe employs high acoustic transmitting titanium at the core and nitinol as the outer member. In another embodiment, the core member may be for example, nitinol and the outer member stainless steel. In another embodiment, the core is tantalum. The outer member could also be formed of a non-metal, e.g., carbon or glass. The ultrasound energy could be used to ablate tissue, enhance delivery of drugs and induce relaxation of tissue, e.g., tumors and in eye surgery e.g., to dissolve cataracts. The acoustic energy can be provided to the probe by axial excitation as illustrated above or by torsional excitation or a combination thereof.

Other Examples

The invention can be embodied in examples too numerous to mention, as will be understood by those skilled in the art. While the preferred embodiment described herein is in the form of a wire, it will be realized that medical components could be of various shapes and configurations including e.g., a radiopaque core and less dense outer member. In other embodiments, the outer member is substantially more radiopaque (e.g., tantalum) compared to the inner member (e.g., stainless steel), for example, for use in guidewire applications to provide a highly radiopaque wire with enhanced flexibility.

Other embodiments are in the following claims.

What is claimed is:

1. A medical device, comprising:
a filter for placement within a channel within a body to filter a body fluid flowing through the channel, the filter including a wire-form member which comprises an outer metal member and a core disposed within the outer metal member, the outer metal member comprising a first metal and the core comprising a second metal different than the first metal,
wherein the second metal has a density greater than the first metal, and the core has a thickness sufficient to enhance the radiopacity of the filter when placed within the body.

2. The medical device of claim 1 wherein the second metal has a density greater than a density of the first metal.

3. The medical device of claim 1 wherein the outer metal member is a longitudinal member and the core is positioned along an axis of the longitudinal member.

4. The medical device of claim 1 wherein the second metal has a density of at least about 9.9 grams per cubic centimeter.

5. The medical device of claim 1 wherein the core comprises a material selected from the group consisting of tungsten, tantalum, rhenium, iridium, silver, gold, bismuth, platinum and alloys thereof.

6. The medical device of claim 1 wherein the core has a modulus of elasticity of about 550 GPa or less.

7. The medical device of claim 1 wherein the core has a modulus of elasticity of about 200 GPa or less.

8. The medical device of claim 1 wherein the outer metal member comprises a material selected from the group consisting of superelastic alloys, precursor alloys of superelastic alloys, stainless steel, and titanium and its alloys.

9. The medical device of claim 1 wherein one of the outer metal member or the core comprises nitinol.

10. The medical device of claim 9 wherein the outer metal member comprises nitinol.

11. The medical device of claim 1 wherein the core comprises from about 1% to about 40% of the cross-sectional dimension of the wire-form member.

12. The medical device of claim 11 wherein the core is at least about 25% of the cross-sectional dimension of the wire-form member.

13. The medical device of claim 12 wherein the core comprises at most about 28% of the cross-sectional dimension of the wire-form member.

14. The medical device of claim 1 wherein the cross-sectional dimension of the wire-form member is less than about 0.025 inch.

15. The medical device of claim 14 wherein the outer metal member has a cross-section of about 0.0045 to about 0.008 inch and the core has a cross section of about 0.0014 to 0.00195 inch.

16. The medical device of claim 1 wherein the core comprises a solid metallic member.

17. The medical device of claim 1 wherein the outer metal member and the core are of circular cross-sectional configuration.

18. The medical device of claim 1 wherein the core contacts the sheath.

19. The medical device of claim 1 wherein the filter includes a conical clot capturing portion formed of the wire-form member.

20. The medical device of claims 1 or 19 wherein the filter includes a lumen wall engaging portion formed of the wire-form member.

21. A medical device, comprising:
a vascular filter for placement in a blood vessel to filter clots in blood flowing through the blood vessel within the body, the filter including a wire-form member which comprises an outer metal member and a core disposed within the outer metal member, the outer metal member comprising a first metal having a density less than about 9.9 grams per cubic centimeter, and the core comprising a second metal having a density greater than 9.9 grams per cubic centimeter,
wherein the core has a thickness suffiecient to enhance the radiopacity of the filter when places within the body.

22. The medical device of claim 21 wherein the core comprises from about 10% to about 50% of the cross-sectional dimension of the wire-form member.

23. The medical device of claim 21 wherein the second metal comprises tantalum.

24. The medical device of claim 21 wherein the outer metal member comprises nitinol.

25. The medical device of claim 21 wherein a cross sectional dimension of the wire-form member is at most about 0.025 inch.

26. The medical device of claim 25 wherein the outer metal member has a cross-section of about 0.0045 to 0.008 inch and the core has a cross section of about 0.0014 to 0.00195 inch.

27. The medical device of claim 21 wherein the core contacts the sheath.

28. The medical device of claim 21 wherein the vascular filter includes a conical clot capturing portion formed of the wire-form member.

29. The medical device of claims 21 or 28 wherein the vascular filter includes a lumen wall engaging portion formed of the wire-form member.

30. A medical device, comprising:
   a filter for filtering a body fluid flowing through a channel in the body, the filter including a wire-form member which comprises a core and a metal sheath intimately surrounding the core, the core having a first thickness and comprising a first metal and the metal sheath having a second thickness different than the first thickness and comprising a second metal different than the first metal, the second metal having a lower density and a greater elasticity than the first metal,
   wherein the core has a thickness sufficient to enhance the radiopacity of the filter when placed within the body.

31. The medical device of claim 30 wherein a combined effect of the thickness of the first and second metals is to enhance radio-opacity of the medical device to provide improved fluoroscopic or x-ray visualization of the medical device in the body while a combined effect of the elasticity of the first and second metals is to impart sufficient elasticity to enable the medical device to elastically self-recover from its characteristic deformed configuration.

32. The medical device of claim 30 wherein the filter includes a conical clot capturing portion formed of the wire-form member.

33. The medical device of claims 30 or 32 wherein the filter includes a lumen wall engaging portion formed of the wire-form member.

34. The medical device of claim 30 wherein the core contacts the metal sheath.

35. A medical device, comprising:
   a filter for placement within a channel within a body to filter a body fluid flowing through the channel, the filter comprising an outer metal member and a core disposed within the outer metal member, the outer metal member comprising a first metal and the core comprising a second metal different than the first metal,
   wherein the second metal has a density greater than the first metal, and the core has a thickness sufficient to enhance the radiopacity of the filter when placed within the body.

* * * * *